(12) United States Patent
Miyachi (10) Patent No.: US 8,672,847 B2
(45) Date of Patent: Mar. 18, 2014

(54) ULTRASOUND DIAGNOSTIC APPARATUS AND METHOD

(75) Inventor: Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/277,287

(22) Filed: Oct. 20, 2011

(65) Prior Publication Data

US 2012/0116229 A1 May 10, 2012

(30) Foreign Application Priority Data

Nov. 10, 2010 (JP) ................................. 2010-251505

(51) Int. Cl.
*A61B 8/00* (2006.01)
(52) U.S. Cl.
USPC .......................................... 600/437; 600/442
(58) Field of Classification Search
USPC ................................................. 600/437–469
See application file for complete search history.

(56) References Cited

U.S. PATENT DOCUMENTS

| | | | |
|---|---|---|---|
| 7,374,538 B2 * | 5/2008 | Nightingale et al. ......... | 600/443 |
| 7,744,537 B2 * | 6/2010 | Kanai et al. ................... | 600/453 |
| 2001/0016686 A1 | 8/2001 | Okada et al. | |
| 2004/0167403 A1 * | 8/2004 | Nightingale et al. ......... | 600/437 |
| 2004/0260180 A1 * | 12/2004 | Kanai et al. ................... | 600/449 |
| 2007/0219447 A1 * | 9/2007 | Kanai et al. ................... | 600/450 |
| 2008/0021318 A1 * | 1/2008 | Kato et al. ..................... | 600/437 |
| 2009/0030324 A1 * | 1/2009 | Kato et al. ..................... | 600/459 |
| 2009/0143675 A1 * | 6/2009 | Suzuki et al. ................. | 600/438 |
| 2010/0016721 A1 * | 1/2010 | Kanai et al. ................... | 600/443 |
| 2010/0113930 A1 * | 5/2010 | Miyachi ........................ | 600/443 |
| 2010/0185090 A1 * | 7/2010 | Suzuki et al. ................. | 600/443 |
| 2010/0312110 A1 * | 12/2010 | Suzuki et al. ................. | 600/443 |

FOREIGN PATENT DOCUMENTS

| | | |
|---|---|---|
| JP | 2001-299752 A | 10/2001 |
| JP | 2005-074146 A | 3/2005 |
| JP | 2006020801 A | 1/2006 |
| JP | 2006115937 A | 5/2006 |
| JP | 2009039258 A | 2/2009 |

OTHER PUBLICATIONS

Notification of Reasons for Refusal, dated Apr. 9, 2013, issued in corresponding JP Application No. 2010-251505, 7 pages in English and Japanese.

* cited by examiner

*Primary Examiner* — Sanjay Cattungal
(74) *Attorney, Agent, or Firm* — Sughrue Mion, PLLC (57) ABSTRACT

An ultrasound diagnostic apparatus comprises: a detector for detecting a direction of radial expansion/contraction of a vascular wall associated with a heartbeat in a long-axis image of the vascular wall based on amplitude information of reception signals outputted from an ultrasound probe when a first ultrasonic beam is transmitted and received to and from a blood vessel of a subject through the ultrasound probe by a transmitter/receiver; a controller for controlling the transmitter/receiver so as to transmit and receive a second ultrasonic beam parallel to the detected vascular wall expansion/contraction direction through the ultrasound probe; a tracker for tracking a movement of the vascular wall using amplitude information and phase information of the reception signals outputted from the ultrasound probe when the second ultrasonic beam is transmitted and received; and a calculator for calculating elastic characteristics of the vascular wall based on the tracked vascular wall movement.

9 Claims, 6 Drawing Sheets

ULTRASOUND DIAGNOSTIC APPARATUS AND METHOD

BACKGROUND OF THE INVENTION

The present invention relates to an ultrasound diagnostic apparatus and an ultrasound diagnostic method and particularly to an ultrasound diagnostic apparatus and an ultrasound diagnostic method for measuring the elastic characteristics of a vascular wall.

Conventionally, ultrasound diagnostic apparatus using ultrasound images are employed in the medical field. In general, this type of ultrasound diagnostic apparatus comprises an ultrasound probe having a built-in transducer array and an apparatus body connected to the ultrasound probe. The ultrasound probe transmits ultrasonic waves toward a subject, receives ultrasonic echoes from the subject, and the apparatus body electrically processes the reception signals to generate an ultrasound image and obtain various information on diseases.

The site of a subject to be ultrasonically examined varies with the kind of disease: in the case of a circulatory disease such as cerebral infarction, for example, carotid arteries are tentatively examined because plaques are liable to develop there. In such ultrasonic diagnosis of carotid arteries, the thickness of a plaque and the elastic characteristics of a vascular wall are measured to obtain information on, for example, the degree to which blood vessel stenosis has progressed and the ease with which the plaque may rupture. In order to obtain such information accurately, an ultrasonic beam is preferably allowed to enter a vascular wall at right angles thereto to accurately detect small changes occurring in the vascular wall as the heart beats. However, because the carotid arteries often do not lie parallel to the body surface in places where plaques tend to develop (where a common carotid artery divides into an internal carotid artery and en external carotid artery), allowing the ultrasonic beam to enter a vascular wall at right angles thereto was a difficult task.

JP 2001-299752 A, for example, describes an ultrasound diagnostic apparatus wherein an ultrasonic beam is steered to transmit the ultrasonic beam in various directions in order to select a direction in which a reflected ultrasonic echo exhibits the maximal amplitude as a direction in which the ultrasonic beam enters a vascular wall at right angles.

JP 2005-074146 A describes an ultrasound diagnostic apparatus wherein an ultrasonic beam is steered to pass through the center of a blood vessel so that the ultrasonic beam intersects the blood vessel at right angles.

SUMMARY OF THE INVENTION

The ultrasound diagnostic apparatus described in JP 2001-299752 A judges whether an ultrasonic beam enters a vascular wall at right angles from the attained maximal amplitude and therefore permits accurate selection of a direction in which the ultrasonic beam enters a blood vessel at right angles where the blood vessel has a consistent wall thickness. However, where the blood vessel thickness is not consistent because of, for example, plaques, an inclined plane is formed in the vascular wall around the plaques, and the ultrasonic echo resulting from the ultrasonic beam entering the inclined plane at right angles also exhibits the maximal amplitude. As a result, high-accuracy measuring of the elastic characteristics of the vascular wall based on the echo from the carotid artery may be made impossible.

The ultrasound diagnostic apparatus described in JP 2005-074146 A determines the center of a blood vessel by approximating the vascular wall with circles in contact with the vascular wall. Accordingly, an ultrasonic beam can be so directed to intersect the vascular wall at right angles where the blood vessel has a consistent wall thickness. However, in a vascular wall whose thickness is not consistent or in a cross section taken along the central axis of the blood vessel, determining the center of the blood vessel is difficult and, therefore, elastic characteristics of the vascular wall may not be accurately measured based on echoes from a carotid artery.

An object of the present invention is to provide an ultrasound diagnostic apparatus and method that resolve such problems of the past, and can measure the elastic characteristics of a vascular wall with high accuracy.

An ultrasound diagnostic apparatus according to the present invention comprises:

an ultrasound probe;

a transmitter/receiver for transmitting and receiving an ultrasonic beam to and from a subject through the ultrasound probe;

an image producer for producing an ultrasound image based on reception signals outputted from the ultrasound probe;

a vascular wall expansion/contraction direction detector for detecting a direction of radial expansion/contraction of a vascular wall associated with a heartbeat in a long-axis image of the vascular wall based on amplitude information of the reception signals outputted from the ultrasound probe when a first ultrasonic beam is transmitted and received to and from a blood vessel of the subject through the ultrasound probe;

a transmission/reception controller for controlling the transmitter/receiver so as to transmit and receive a second ultrasonic beam parallel to the vascular wall expansion/contraction direction detected by the vascular wall expansion/contraction direction detector through the ultrasound probe;

a vascular wall tracker for tracking a movement of the vascular wall using amplitude information and phase information of the reception signals outputted from the ultrasound probe when the second ultrasonic beam is transmitted and received; and a vascular wall elastic characteristics calculator for calculating elastic characteristics of the vascular wall based on the vascular wall movement tracked by the vascular wall tracker.

An ultrasound diagnostic method according to the present invention comprises the steps of:

transmitting and receiving through an ultrasound probe a first ultrasonic beam to and from a blood vessel of a subject;

detecting a direction of radial expansion/contraction of a vascular wall associated with a heartbeat in a long-axis image of the vascular wall based on amplitude information of reception signals outputted from an ultrasound probe when the first ultrasonic beam is transmitted and received;

transmitting and receiving through the ultrasound probe a second ultrasonic beam parallel to the detected vascular wall expansion/contraction direction to and from the blood vessel of the subject;

tracking a movement of the vascular wall using amplitude information and phase information of the reception signals outputted from the ultrasound probe when the second ultrasonic beam is transmitted and received; and calculating elastic characteristics of the vascular wall based on the tracked vascular wall movement.

DETAILED DESCRIPTION OF THE INVENTION

Embodiments of the present invention will be described below based on the appended drawings.

Embodiment 1

Figure 1:
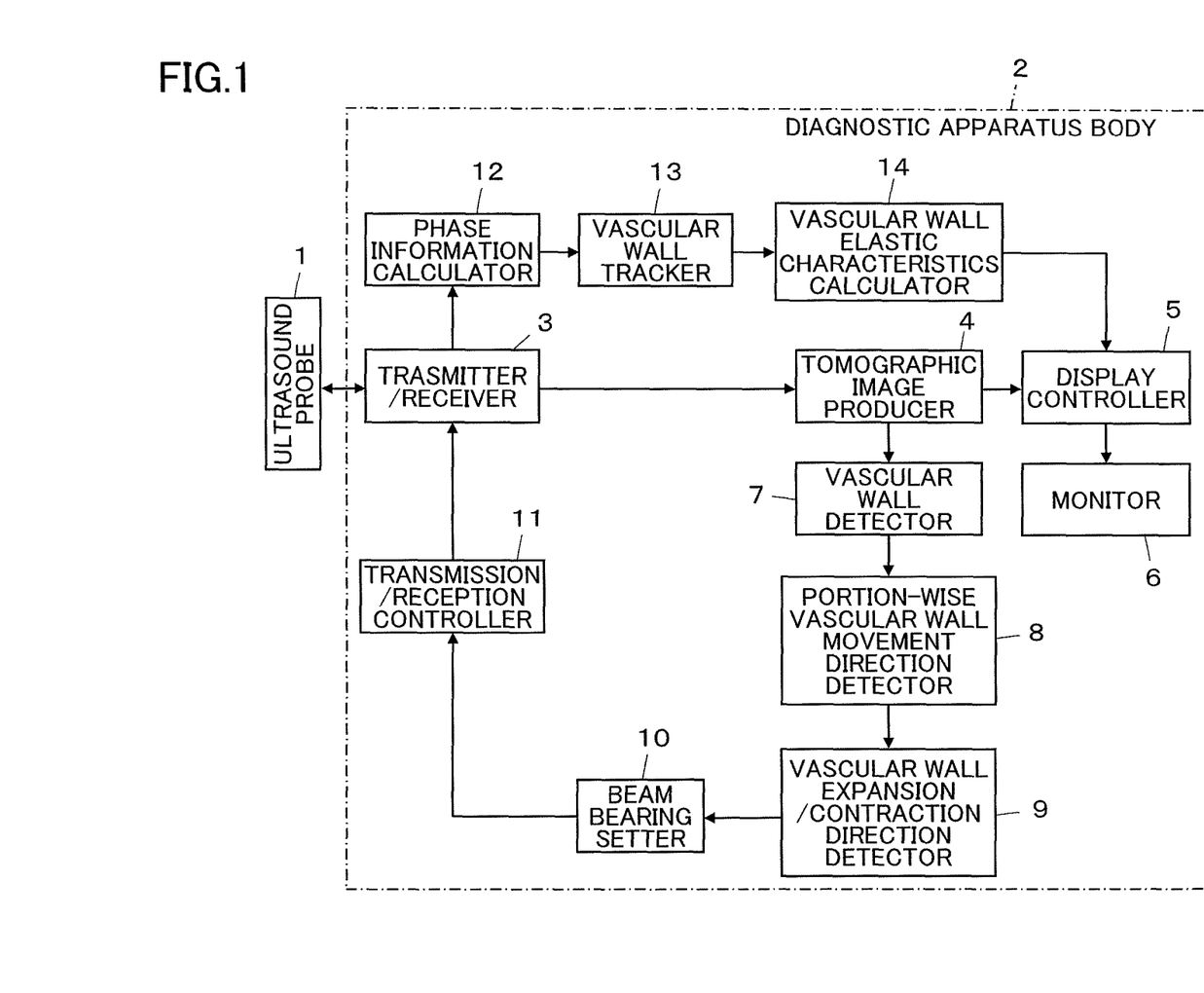
FIG. 1 is a block diagram illustrating an ultrasound diagnostic apparatus according to Embodiment 1 of the invention.

FIG. 1 illustrates a configuration of the ultrasound diagnostic apparatus according to Embodiment 1 of the invention. The ultrasound diagnostic apparatus comprises an ultrasound probe 1 for transmission and reception of ultrasonic waves and a diagnostic apparatus body 2 connected to the ultrasound probe 1. The diagnostic apparatus body 2 controls transmission and reception of ultrasonic waves by the ultrasound probe 1, produces image data representing an ultrasound image based on acquired reception signals, calculates elastic characteristics of a vascular wall, and displays a strain image.

The ultrasound probe 1 is a probe of, for example, convex scan type, linear scan type, or sector scan type, brought into contact with a subject. The ultrasound probe 1 comprises a plurality of ultrasound transducers arranged one-dimensionally or two-dimensionally. The ultrasound transducers transmit ultrasonic waves toward a subject based on applied actuation signals and receives ultrasonic echoes bounced off the subject to output reception signals.

Each of the ultrasound transducers is composed of an oscillator including a piezoelectric body made of, for example, a piezoelectric ceramic typified by PZT (lead zirconate titanate) or a piezoelectric polymer typified by PVDF (polyvinylidene difluoride) and an electrode provided on both ends of the piezoelectric body. Application of a pulsed or continuous-wave voltage to electrodes of the oscillators causes the piezoelectric bodies to contract. The contraction causes the oscillators to produce pulsed or continuous-wave ultrasonic waves, which are combined to form an ultrasonic beam. Upon reception of propagating ultrasonic waves, the oscillators contract to produce electric signals. The electric signals are outputted as reception signals of ultrasonic waves.

The diagnostic apparatus body 2 comprises a transmitter/receiver 3 connected to the ultrasound probe 1. The transmitter/receiver 3 is connected to a tomographic image producer 4, which in turn is connected via a display controller 5 to a monitor 6. The tomographic image producer 4 is connected to a transmission/reception controller 11 via a vascular wall detector 7, a portion-wise vascular wall movement direction detector 8, a vascular wall expansion/contraction direction detector 9, and a beam bearing setter 10 in order. The transmission/reception controller 11 is connected to the transmitter/receiver 3. The transmitter/receiver 3 is also connected to a phase information calculator 12, a vascular wall tracker 13, and a vascular wall elastic characteristics calculator 14 in order. The vascular wall elastic characteristics calculator 14 is connected to the display controller 5.

The transmission/reception controller 11 sets directions of ultrasonic beam transmission and ultrasonic echo reception by the ultrasound probe 1 in sequence and has a transmission control function for selecting a transmission delay pattern according to a set transmission direction and a reception control function for selecting a reception delay pattern according to a set reception direction.

The transmission delay pattern is a pattern of delay times allotted to actuation signals for the respective ultrasound transducers to form an ultrasonic beam in a desired direction with ultrasonic waves transmitted from a plurality of ultrasound transducers of the ultrasound probe 1; the reception delay pattern is a pattern of delay times allotted to reception signals for the respective ultrasound transducers to extract ultrasonic echoes traveling from a desired direction with ultrasonic waves received by a plurality of ultrasound transducers. A plurality of transmission delay patterns and a plurality of reception delay patterns are stored in a storage unit in the transmission/reception controller 11 and selected and used as appropriate.

The transmitter/receiver 3 incorporates a transmission circuit and a reception circuit. The transmission circuit comprises a plurality of channels and produces a plurality of actuation signals applied to the plurality of ultrasound transducers of the ultrasound probe 1. In that process, the actuation signals can be given respective delays based on the transmission delay pattern selected by the transmission/reception controller 11. The transmission circuit may adjust the delay amounts of the actuation signals before supplying the signals to the ultrasound probe 1 so that the ultrasonic waves supplied from the plurality of ultrasound transducers form an ultrasonic beam or may supply a plurality of actuation signals to the ultrasound probe 1 so that the ultrasonic waves transmitted all at once from the plurality of ultrasound transducers reach the entire imaged region of the subject.

The reception circuit of the transmitter/receiver 3 comprises a plurality of channels to receive and amplify a plurality of analog reception signals outputted from the plurality of respective ultrasound transducers and convert the signals into digital reception signals. In that process, the transmitter/receiver 3 provides the plurality of reception signals with respective delays based on the reception delay pattern selected by the transmission/reception controller 11 and adds up the reception signals to perform reception focusing processing. By this reception focusing processing, a sound ray signal (sound ray data) in which the focal points of the ultrasonic echoes are made to converge is generated.

Next, the sound ray data undergoes envelop detection processing by means of, for example, low pass filter processing, followed by attenuation correction according to the distance depending on the depth of the ultrasonic wave reflection position using STC (Sensitivity Time gain Control).

The sound ray data thus processed are sequentially stored in a data memory having a sufficient memory capacity for accumulating sound ray data for a plurality of frames. Having an image data producing function, the reception circuit is inputted with sound ray data directly supplied in a live mode and sound ray data supplied from the data memory in a freeze mode, and performs pre-processing such as Log compression and gain adjustment on these sound ray data to produce image data, which are outputted to the tomographic image producer 4.

The tomographic image producer 4 converts the image data of an ultrasound image supplied from the reception circuit of the transmitter/receiver 3 into image data compatible with the ordinary television signal scanning method through raster conversion and performs necessary image processing such as gradation processing before supplying the data to the display controller 5. Further, the tomographic image producer 4 supplies the image data of the ultrasound image to the vascular wall detector 7.

The display controller 5 causes the monitor 6 to display an ultrasound diagnostic image based on the image data supplied from the tomographic image producer 4. The monitor 6 includes a display device such as an LCD, for example, and displays an ultrasound diagnostic image under the control by the display controller 5.

The vascular wall detector 7 detects the position of a vascular wall by, for example, image-processing the image data supplied from the tomographic image producer 4. The portion-wise vascular wall movement direction detector 8 divides the vascular wall in an ultrasound image detected by the vascular wall detector 7 into a plurality of portions and detects the direction in which each of the vascular wall portions moves in association with the heartbeat based on the position of each of the divided portions varying from frame to frame. The movement direction of each of the vascular wall portions is detected by, for example, the pattern matching method. The vascular wall expansion/contraction direction detector 9 detects the direction of expansion/contraction of a vascular wall in a radial direction associated with the heartbeat based on the movement direction of each of the vascular wall portions detected by the vascular wall movement direction detector 8. The beam bearing setter 10 sets the bearing of the ultrasonic beam so that the ultrasonic beam is transmitted parallel to the direction of the vascular wall expansion/contraction direction detected by the vascular wall expansion/contraction direction detector 9.

The transmission/reception controller 11 sets a transmission delay pattern such that the ultrasound probe 1 transmits an ultrasonic beam in a direction set by the beam bearing setter 10 and outputs the transmission delay pattern to the transmitter/receiver 3. The ultrasound probe 1 transmits the ultrasonic beam parallel to the vascular wall expansion/contraction direction based on the transmission delay pattern set by the transmission controller 11.

The phase information calculator 12 is inputted via the transmitter/receiver 3 with the reception signals from the ultrasound probe 1 that were produced in transmission and reception of an ultrasonic beam parallel to the vascular vessel expansion/contraction direction. The phase information calculator 12 calculates phase information based on the reception signals from the transmitter/receiver 3.

The vascular wall tracker 13 uses amplitude information and the phase information of the reception signals entered via the phase information calculator 12 to accurately track the movement of the vascular wall. The tracking may be performed by, for example, a method described in JP 3652791B.

The vascular wall elastic characteristics calculator 14 calculates the elastic characteristics of a vascular wall based on the vascular wall movement tracked by the vascular wall tracker 13, produces strain image data, and allows the monitor 6 to display a strain image through the display controller 5.

Figure 2:
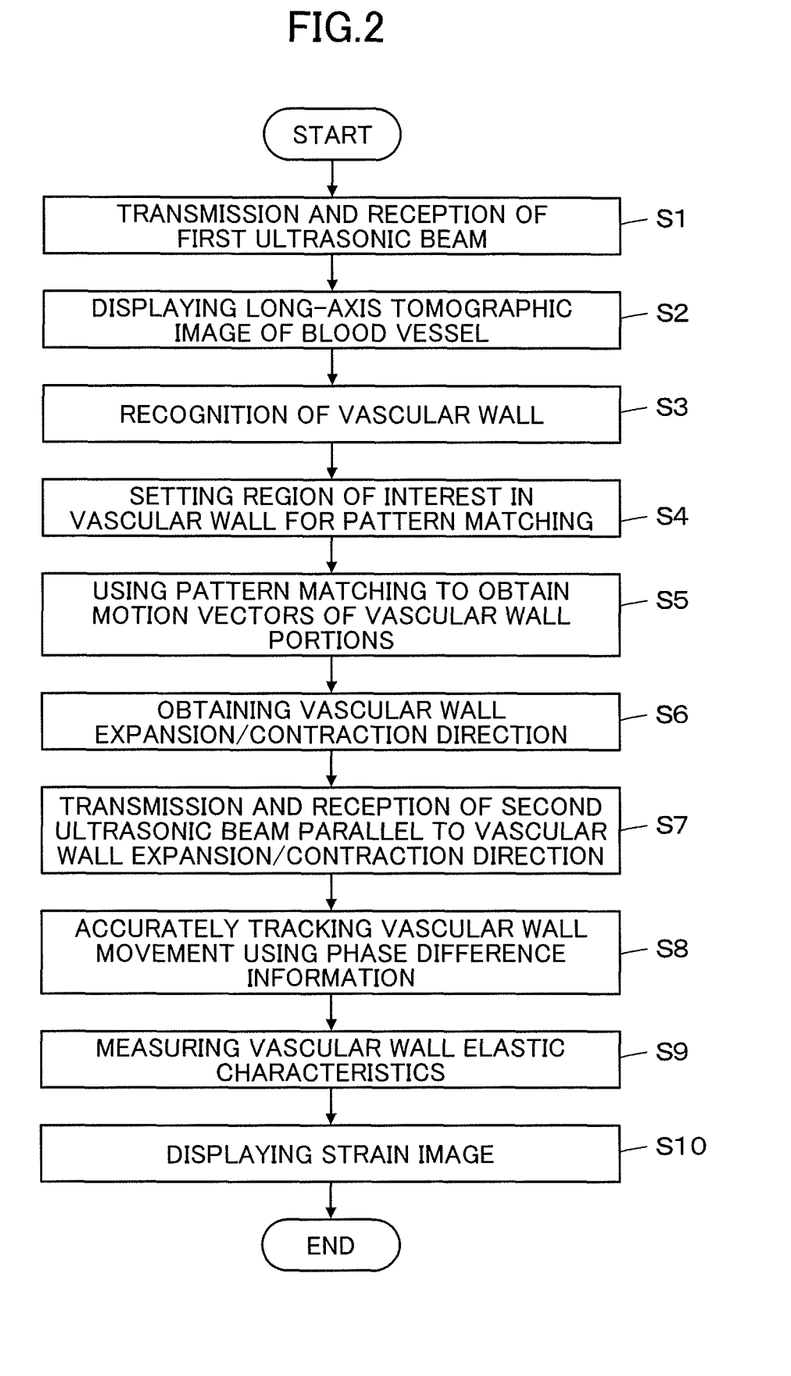
FIG. 2 is a flow chart representing the operation of the ultrasound diagnostic apparatus according to Embodiment 1.

Next, the operation of Embodiment 1 will be described referring to the flowchart of FIG. 2.

Figure 3:
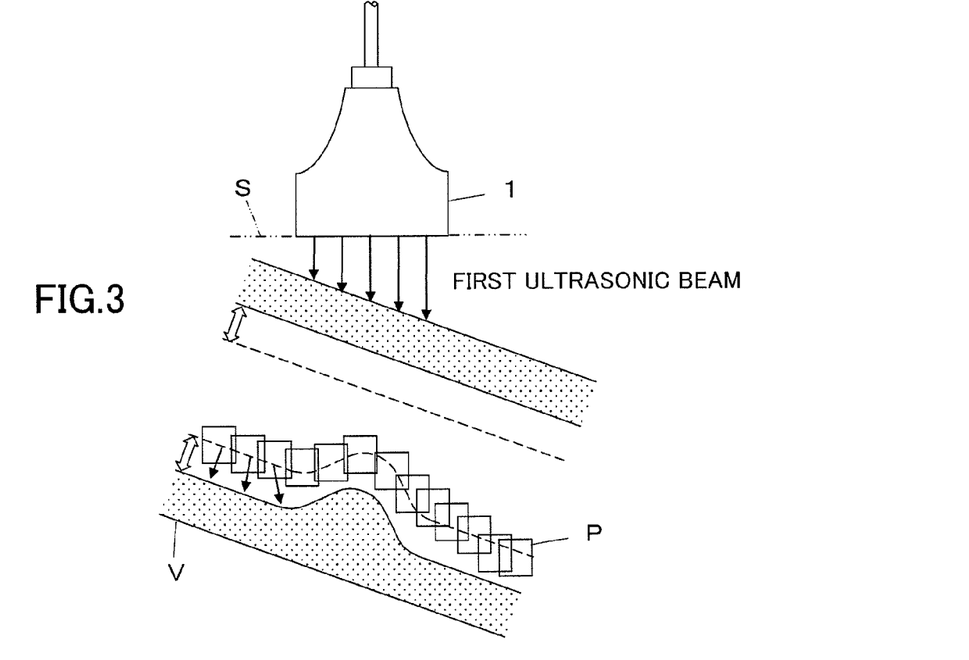
FIG. 3 is a view illustrating how the first ultrasonic beam is transmitted to an expanding and contracting vascular wall.

First, as illustrated in FIG. 3, upon being placed in contact with a body surface S in step S1, the ultrasound probe 1 transmits a first ultrasonic beam in response to the actuation signals from the transmission circuit of the transmitter/receiver 3 of the diagnostic apparatus body 2 in a direction perpendicular to the body surface S. The first ultrasonic beam transmitted from the ultrasound probe 1 enters a blood vessel V along the long axis thereof and is reflected by the vascular wall so that the ultrasonic echoes thereof are received by the plurality of ultrasound transducers of the ultrasound probe 1. The reception signals corresponding to the received ultrasonic echoes are outputted from the ultrasound probe 1 to the reception circuit of the transmitter/receiver 3 and digitalized by the reception circuit, whereupon image data of the tomographic image along the long axis of the blood vessel V are produced based on the intensity (amplitude) of the digital signals in each frame. The image data of a tomographic image thus produced are outputted from the transmitter/receiver 3 to the tomographic image producer 4.

In step S2, the image data along the long axis of the blood vessel V entered into the tomographic image producer 4 undergo necessary image processing such as gradation processing and are outputted to the display controller 5 so that the monitor 6 displays a long-axis tomographic image of the blood vessel V. The tomographic image producer 4 outputs the image data of the long-axis tomographic image to the vascular wall detector 7. In step S3, the vascular wall detector 7 uses the difference in amplitude between the vascular wall and the blood vessel lumen in the image data of the entered the long-axis tomographic image to recognize the position of the vascular wall, and in step S4, sets a region of interest (ROI) for pattern matching in the recognized position of the vascular wall. Specifically, after converting the long-axis tomographic image into a blurred image, the vascular wall detector 7 performs binarization processing based on the fact that the amplitude in a blood vessel lumen is smaller than in the vascular wall in the long-axis tomographic image and sets a region of interest in each frame considering a depth range of, say, about 2 mm from the black and white edge portion as the vascular wall.

The image data of the long-axis tomographic image in which a region of interest has been set are outputted from the vascular wall detector 7 to the portion-wise vascular wall movement direction detector 8. As illustrated in FIG. 3, the portion-wise vascular wall movement direction detector 8 uses the long-axis tomographic image in which a region of interest has been set to divide the region of interest into a plurality of portions P. The portions P in the region of interest vary in position in each frame as the vascular wall expands and contracts radially in association with the heartbeat. In step S5, the portion-wise vascular wall movement direction detector 8 detects the motion vector of each portion P in the region of interest varying in each frame by pattern matching method. In other words, the portion-wise vascular wall movement direction detector 8 obtains the direction of positional variation of each portion P associated with the heartbeat as motion vector.

Figure 4:
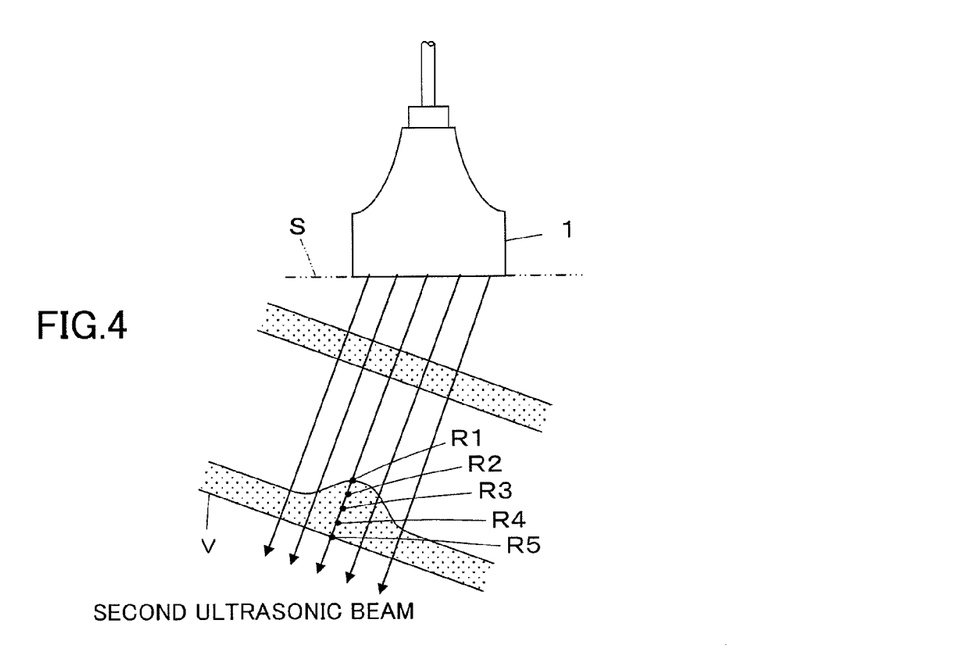
FIG. 4 is a view illustrating how the second ultrasonic beam is transmitted in a direction in which a vascular wall expands and contracts.

The portion-wise vascular wall movement direction detector 8 outputs the motion vector of each portion P of the vascular wall to the vascular wall expansion/contraction direction detector 9. In step S6, the vascular wall expansion/contraction direction detector 9 averages the motion vectors of the portions P of the vascular wall or use some other method to obtain the radial vascular wall expansion/contraction direction associated with the heartbeat. The vascular wall expansion/contraction direction thus obtained is outputted from the vascular wall expansion/contraction direction detector 9 to the beam bearing setter 10, whereupon the beam bearing setter 10 sets the direction of the second ultrasonic beam so that the ultrasound probe 1 transmits the second ultrasonic beam parallel to the expansion/contraction direction. The set bearing of the second ultrasonic beam is outputted from the beam bearing setter 10 to the transmission/reception controller 11, which in turn sets a transmission delay pattern based on the bearing of the second ultrasonic beam. The transmission delay pattern is outputted from the transmission controller 11 to the transmission circuit of the transmitter/receiver 3, and the transmission circuit supplies the ultrasound probe 1 with actuation signals based on the transmission delay pattern. Thus, in step S7, the ultrasound probe 1 transmits the second ultrasonic beam steered in a direction parallel to the vascular wall expansion/contraction direction as illustrated in FIG. 4.

Thus, because the bearing in which the second ultrasonic beam is transmitted is set so as to be parallel to the vascular wall expansion/contraction direction based on the vascular wall amplitude information obtained using the first ultrasonic beam, the second ultrasonic beam can be steered parallel to the vascular wall expansion/contraction direction even when the vascular thickness is inconsistent because of, for example, a plaque.

Figure 5:
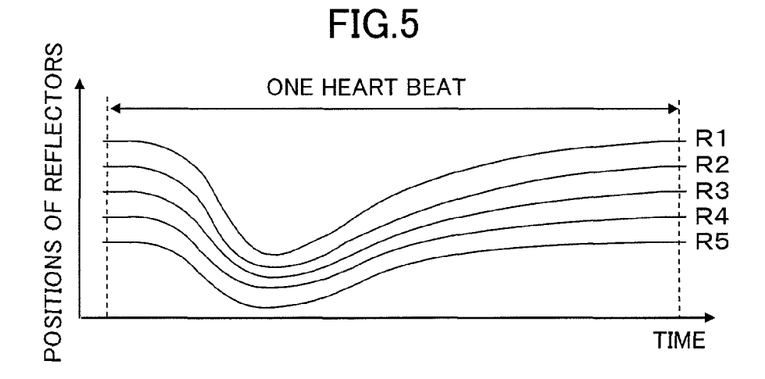
FIG. 5 is a graph illustrating positional variation of reflection points in one heartbeat.

The second ultrasonic beam transmitted from the ultrasound probe 1 steered parallel to the vascular wall expansion/contraction direction is reflected off a reflection point that is located in, for example, an interface between tissues having different characteristics such as elastic characteristics in a vascular wall. Suppose, for example, that, as illustrated in FIG. 4 the second ultrasonic beam entering a plaque formed in a vascular wall on the farther side from the ultrasound probe 1 is reflected off the reflection points R1 to R5 in the vascular wall, the ultrasonic echoes from the reflection points R1 to R5 are received by the ultrasound probe 1. The reception signals corresponding to the ultrasonic echoes from the reflection points R1 to R5 received by the ultrasound probe 1 are outputted from the ultrasound probe 1 to the reception circuit of the transmitter/receiver 3, whereupon the reception circuit digitalizes the reception signals and obtains the amplitude information thereof, which is outputted from the transmitter/receiver 3 to the phase information calculator 12. The phase information calculator 12 calculates the phase information of the reception signals corresponding to the ultrasonic echoes from the reflection points R1 to R5 and supplies the amplitude information and the phase information to the vascular wall tracker 13. The vascular wall tracker 13 accurately tracks the inter-frame movements of the reflection points R1 to R5 in the vascular wall in step S8. By the tracking, the variations in position of the reflection points R1 to R5 in, for example, one heartbeat are obtained as illustrated in FIG. 5.

Figure 6A:
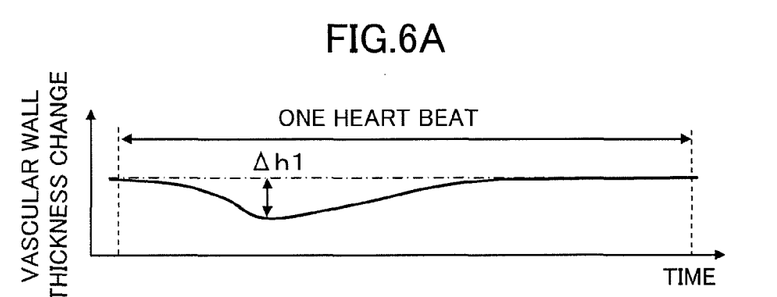
FIG. 6A is a graph illustrating variation in thickness between reflection points R1 and R2 in one heartbeat.
Figure 6B:
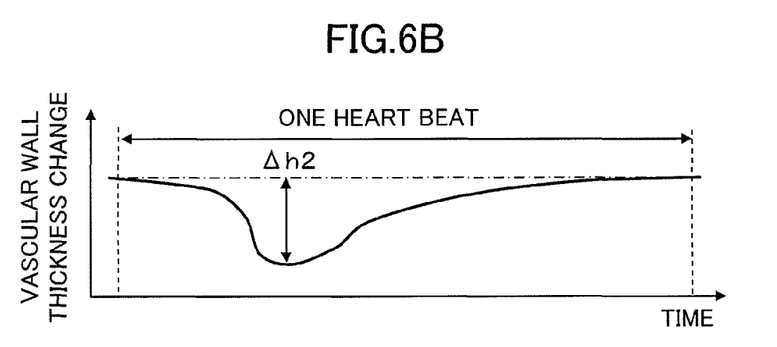
FIG. 6B is a graph illustrating variation in thickness between reflection points R2 and R3 in one heartbeat.

The tracked movements of the reflection points R1 to R5 in the vascular wall are outputted from the vascular wall tracker 13 to the vascular wall elastic characteristics calculator 14, which extracts the differences in position (phase) between adjacent reflection points based on the tracked movements of the reflection points R1 to R5 in the vascular wall to calculate the thicknesses and obtain time-varying thickness waveforms. As illustrated in FIG. 6A, for example, a positional difference between the reflection points R1 and R2 for one heartbeat is used to obtain a waveform representing a variation in thickness over time between these reflection points, and, as illustrated in FIG. 6B, a positional difference between the reflection points R2 and R3 for one heartbeat is used to obtain a waveform representing a variation in thickness over time between these reflection points. Based on the obtained waveforms each representing a time-varying thickness between adjacent reflection points, an amount of strain $\epsilon_i$ occurring between adjacent reflection points in a vascular wall radius direction is computed using the following formula (1)

$$\epsilon_i = \Delta h_i / h_{di} \quad (1)$$

wherein $h_{di}$ is a thickness between adjacent reflection points toward the end of a heart expansion period when the vascular wall is thickest; $\Delta h_i$ is a maximum of variation in thickness between adjacent reflection points in a heart contraction period when the thickness is smallest during one heartbeat. Based on the formula (1), comparison of $\Delta h_1$ between the reflection points R1 and R2 of FIG. 6A with $\Delta h_2$ between the reflection points R2 and R3 of FIG. 6B shows that $\Delta h_2$ is greater than $\Delta h_1$, suggesting that the tissue between the reflection points R1 and R2 is harder than the tissue between the reflection points R2 and R3. Thus, the amount of strain is calculated as vascular wall elastic characteristics by the vascular wall elastic characteristics calculator 14 in step S9.

Figure 7:
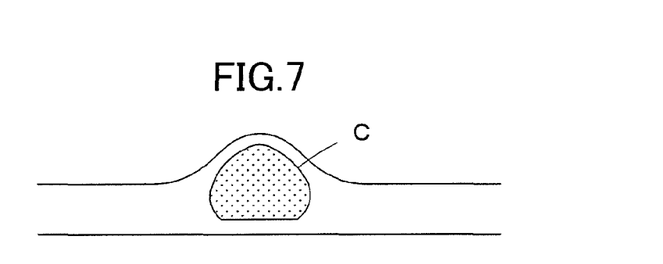
FIG. 7 is a view illustrating an image of a strain caused by a plaque.

Subsequently, through image processing whereby the amounts of strain between adjacent reflection points in the blood vessel V are assigned corresponding colors in a color map, a strain image is displayed on the monitor 6 through the intermediary of the display controller 5 in step S10. A strain image as illustrated in FIG. 7, for example, contains a portion C having a great strain at the center of a plaque, suggesting that the central portion C in the plaque contains much lipid that is softer than the portion around it.

This embodiment, whereby the second ultrasonic beam is allowed to enter a blood vessel parallel to the vascular wall, enables a high-accuracy measuring of a small phase change. Further, accurate elastic characteristics obtained provide useful information for clinical medicine that cannot be known from tomographic images.

Elastic characteristics that may be obtained include elastic modulus, strain rate, and stiffness parameter, and the strain image may contain any of these.

The elastic modulus, which may be an elastic modulus $E_{ri}$ in the radial direction of a blood vessel or an elastic modulus $E_{\theta i}$ in the circumferential direction, is obtained using, for example, the following formulae (2) and (3).

$$E_{ri} = \Delta p / (\Delta h_i / h_{di}) \quad (2)$$

$$E_{\theta i} = (r_d / h_d + 1) \Delta p / 2 (\Delta h_i / h_{di}) \quad (3)$$

wherein $r_d$ is the inner radius of the blood vessel toward the end of a heart expansion period, $h_d$ is a vascular wall thickness toward the end of a heart expansion period, $h_{di}$ is a thickness between adjacent reflection points toward the end of a heart expansion period, $\Delta h_i$ is a maximum of variation in thickness between adjacent reflection points in a heart contraction period, $\Delta_p$ is a difference between a blood pressure in a heart contraction period and a blood pressure toward the end of a heart expansion period.

A strain rate $SR_i$ may be obtained from the following formula (4) using $\Delta h_i$, a maximum of variation in thickness between adjacent reflection points in a heart contraction period and $\Delta T$, time from close to the end of a heart expansion period to a heart contraction period.

$$SR_i = \Delta h_i / \Delta T \quad (4)$$

To obtain a stiffness parameter β, first a maximum blood vessel diameter Ds and a minimum blood vessel diameter Dd are obtained as a blood vessel diameter D changes, and a maximum Ps and a minimum Pd of blood pressure reading are obtained by measuring the blood pressure and these values are substituted in a formula (5) below.

$$\beta = \{Log(Ps/Pd)\}/(Ds/Dd-1) \tag{5}$$

Embodiment 2

Figure 8:
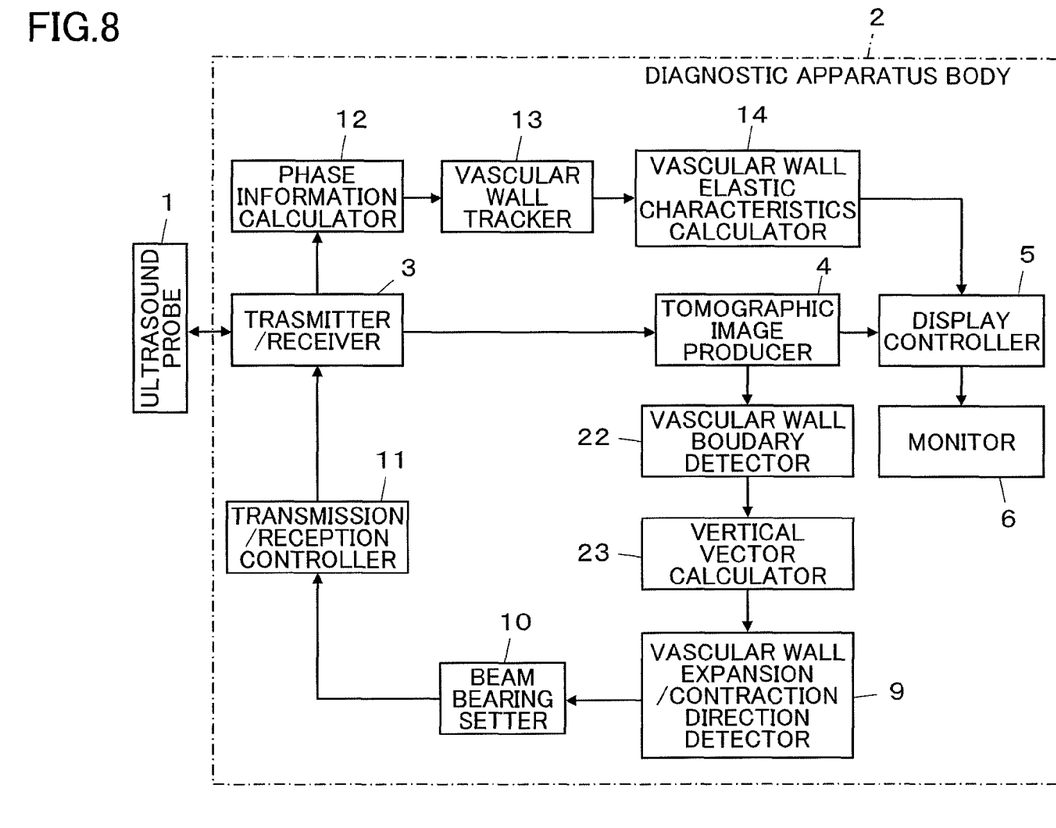
FIG. 8 is a block diagram illustrating an ultrasound diagnostic apparatus according to Embodiment 2.

FIG. 8 illustrates a configuration of the ultrasound diagnostic apparatus according to Embodiment 2. This ultrasound diagnostic apparatus uses a diagnostic apparatus body 21 instead of the diagnostic apparatus body 2 of Embodiment 1 illustrated in FIG. 1. In the diagnostic apparatus body 21, a vascular wall boundary detector 22 and a vertical vector calculator 23 are provided between the tomographic image producer 4 and the vascular wall expansion/contraction direction detector 9 in order instead of the vascular wall detector 7 and the portion-wise vascular wall movement direction detector 8 provided in the diagnostic apparatus body 2 in Embodiment 1.

As in Embodiment 1, the ultrasound probe 1 transmits and receives the first ultrasonic beam to and from a blood vessel of a subject, and the tomographic image producer 4 inputs the image data of a long-axis tomographic image produced based on the reception signals outputted from the ultrasound probe 1 to the vascular wall boundary detector 22. The vascular wall boundary detector 22 uses the difference in amplitude between blood vessel lumen and vascular wall in the entered image data of the long-axis tomographic image to detect the boundary between them and sets a plurality of points on the detected boundary. The image data of the long-axis tomographic image having the points set on the boundary are outputted to the vertical vector calculator 23, which then calculates unit vectors vertical to the boundary at the points set on the boundary. The vascular wall expansion/contraction direction detector 9 adds up the unit vectors at the points set on the boundary calculated by the vertical vector calculator 23 and obtains a direction substantially perpendicular to the boundary to detect the vascular wall expansion/contraction direction.

Based on the blood vessel expansion/contraction direction thus detected, the bearing of the second ultrasonic beam is set, and the second ultrasonic beam is transmitted from and received by the ultrasound probe 1. Subsequently, based on the reception signals from the reception points in the vascular wall obtained using the second ultrasonic beam, the vascular wall tracker 13 accurately tracks the movements of the reflection points in the vascular wall to obtain the positional variations of the reflection points in the vascular wall associated with the heartbeat. Based on the positional variations of the reflection points, the vascular wall elastic characteristics calculator 14 calculates each thickness between adjacent reflection points and calculates time-varying waveforms to obtain vascular wall elastic characteristics using the time-varying waveforms.

This embodiment is capable of accurately measuring a small phase change and obtaining useful information for clinical medicine that cannot be exactly known from tomographic images. Further, because the vascular wall expansion/contraction direction is detected by adding up the unit vectors vertical to the boundary, an accurate detection of the vascular wall expansion/contraction direction is possible even when the movement of a vascular wall caused by the heartbeat is not vertical to the vascular wall.

Embodiment 3

Figure 9:
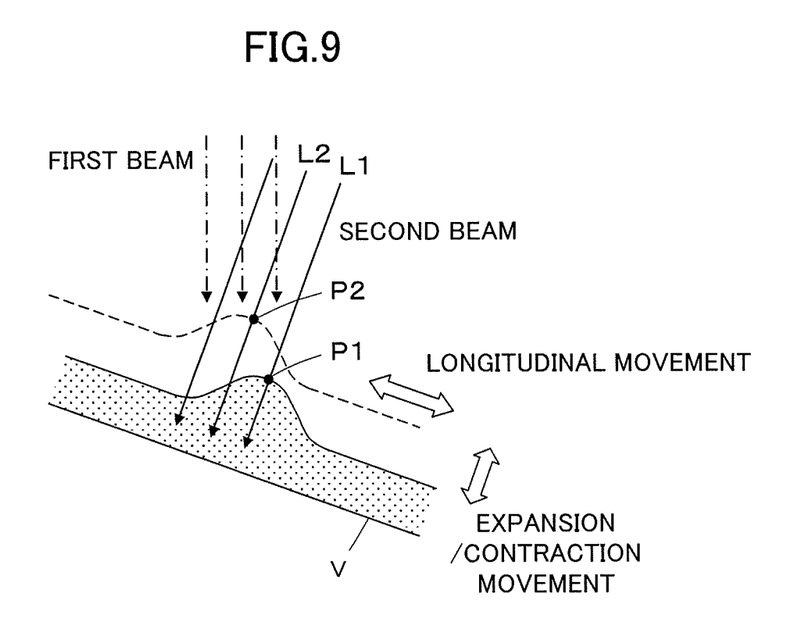
FIG. 9 is a view illustrating how a first ultrasonic beam and a second ultrasonic beam are transmitted in Embodiment 3.

When, as illustrated in FIG. 9, the vascular wall expands and contracts in the radial direction and also moves in a direction perpendicular to the expansion/contraction direction as the heart beats, the tracking of the vascular wall may be achieved by obtaining the vascular wall expansion/contraction direction using the ultrasound diagnostic apparatus according to Embodiment 2 and using the amplitude information and the phase information of the reception signals corresponding to the positions preceding and following the movement.

First, as in Embodiment 2, the ultrasound probe 1 transmits and receives the first ultrasonic beam to and from the blood vessel V of the subject, and the vascular wall boundary detector 22 detects the boundary between the blood vessel lumen and the vascular wall based on the amplitude information of the reception signals outputted from the ultrasound probe 1 and sets a plurality of points on the boundary. Subsequently, the vertical vector calculator 23 calculates unit vectors at the points on the boundary that are vertical to the boundary while the vascular wall expansion/contraction direction detector 9 adds up the unit vectors at the points on the boundary to detect the vascular wall expansion/contraction direction.

Based on the vascular wall expansion/contraction direction thus detected, the bearing of the second ultrasonic beam is set, whereupon the ultrasound probe 1 transmits the second ultrasonic beam composed of a plurality of scan lines parallel to the vascular wall expansion/contraction direction. Suppose that, as illustrated in FIG. 9, the vascular wall expands/contracts and also moves in the longitudinal direction as the heart beats and, accordingly, a given portion of the vascular wall moves from a position P1 to a position P2 so that the position P1 preceding the movement is located on a scan line L1 of the second ultrasonic beam and the position P2 following the movement is located on a scan line L2 of the second ultrasonic beam. The ultrasonic echoes reflected off the given portion of the vascular wall before and after the movement are received by the ultrasound probe 1, which supplies the vascular wall tracker 13 with the reception signals corresponding to the ultrasonic echoes through the transmitter/receiver 3 and the phase information calculator 12.

The vascular wall tracker 13 accurately tracks the vascular wall movement based on the amplitude information and the phase information acquired from the reception signals to obtain the positional variation of the vascular wall associated with the heartbeat. The inter-frame movement of the given position of the vascular wall illustrated in FIG. 9, for example, is accurately tracked based on the amplitude information and the phase information acquired from the reception signals to obtain the position P1 and the position P2 preceding and following the movement respectively, while the scan lines L1 and L2 respectively passing through the positions P1 and P2 out of the scan lines of the second ultrasonic beam are obtained. Subsequently, based on the reception signal obtained from the scan line L1 of the second ultrasonic beam and the reception signal obtained from the scan line L2 of the second ultrasonic beam, the positional variation occurring in the expansion/contraction direction between the points P1 and P2 is calculated from the phase difference between the position P1 of the given portion of the vascular wall preceding the movement and the position P2 of the given portion of the vascular wall following the movement. Thus, the vascular wall tracker 13 calculates the positional variation in the vascular expansion/contraction direction associated with the heartbeat based on the phases of the reception signals obtained from the scan lines corresponding to the respective positions of the portions in the vascular wall preceding and following the movement out of the scan lines of the second ultrasonic beam. The same tracking is carried out for a plurality of reflection points in the vascular wall to obtain the positional variation occurring in the expansion/contraction direction of the reflection points corresponding to, say, one heartbeat.

Based on the positional variations of the reflection points occurring in the vascular wall expansion/contraction direction obtained by the vascular wall tracker 13, the vascular wall elastic characteristics calculator 14 calculates each thickness between adjacent reflection points and calculates time-varying waveforms to obtain vascular wall elastic characteristics using the time-varying waveforms.

This embodiment enables a high-accuracy measuring of a small phase change even when a vascular wall moves in the axial direction of the blood vessel.

What is claimed is:

1. An ultrasound diagnostic apparatus comprising:
   an ultrasound probe;
   a transmitter/receiver for transmitting a first ultrasonic beam to a subject through the ultrasound probe and transmitting a second ultrasonic beam to the subject through the ultrasound probe, and receiving ultrasonic echoes arising from the first ultrasonic beam and ultrasonic echoes arising from the second ultrasonic beam;
   an image producer for producing an ultrasound image based on reception signals outputted from the ultrasound probe;
   a vascular wall expansion/contraction direction detector for detecting a direction of radial expansion/contraction of a vascular wall associated with a heartbeat in a long-axis image of the vascular wall based on amplitude information of the reception signals obtained by receiving the ultrasonic echoes reflected by a blood vessel of the subject when the first ultrasonic beam is transmitted through the ultrasound probe;
   a transmission/reception controller for controlling the transmitter/receiver so as to transmit the first ultrasonic beam in a first direction so that the first ultrasonic beam enters the blood vessel and receive the ultrasonic echoes arising from the first ultrasonic beam and to transmit the second ultrasonic beam in a second direction parallel to the vascular wall expansion/contraction direction detected by the vascular wall expansion/contraction direction detector through the ultrasound probe and receive the ultrasonic echoes arising from the second ultrasonic beam;
   a vascular wall tracker for tracking a movement of the vascular wall using amplitude information and phase information of the reception signals obtained by receiving the ultrasonic echoes arising from the second ultrasonic beam transmitted in the second direction; and
   a vascular wall elastic characteristics calculator for calculating elastic characteristics of the vascular wall based on the vascular wall movement tracked by the vascular wall tracker.

2. The ultrasound diagnostic apparatus according to claim 1, wherein the vascular wall expansion/contraction direction detector detects the vascular wall expansion/contraction direction by pattern matching the position of the vascular wall in each frame based on the amplitude information of the reception signals outputted from the ultrasound probe when the first ultrasonic beam is transmitted and received by the transmitter/receiver.

3. The ultrasound diagnostic apparatus according to claim 1, wherein the vascular wall expansion/contraction direction detector detects a boundary between a blood vessel lumen and the vascular wall based on the amplitude information of the reception signals outputted from the ultrasound probe when the first ultrasonic beam is transmitted and received by the transmitter/receiver and detects a direction substantially perpendicular to the detected boundary as the vascular wall expansion/contraction direction.

4. The ultrasound diagnostic apparatus according to claim 1, wherein when the vascular wall moves in a direction perpendicular to the vascular wall expansion/contraction direction associated with a heartbeat, the vascular wall tracker tracks the vascular wall movement using the amplitude information and the phase information of the reception signals corresponding to respective positions preceding and following the movement.

5. An ultrasound diagnostic method comprising the steps of:
   transmitting through an ultrasound probe a first ultrasonic beam to a subject in a first direction so that the first ultrasonic beam enters the blood vessel, and receiving ultrasonic echoes reflected by a blood vessel of the subject when the first ultrasonic beam is transmitted through the ultrasound probe;
   detecting a direction of radial expansion/contraction of a vascular wall associated with a heartbeat in a long-axis image of the vascular wall based on amplitude information of reception signals obtained by receiving the ultrasonic echoes arising from the first ultrasonic beam;
   transmitting through the ultrasound probe a second ultrasonic beam in a second direction parallel to the detected vascular wall expansion/contraction direction, and receiving through the ultrasound probe the ultrasonic echoes arising from the second ultrasonic beam;
   tracking a movement of the vascular wall using amplitude information and phase information of the reception signals obtained by receiving the ultrasonic echoes arising from the second ultrasonic beam transmitted in the second direction; and
   calculating elastic characteristics of the vascular wall based on the tracked vascular wall movement.

6. The ultrasound diagnostic method according to claim 5, wherein the vascular wall expansion/contraction direction is detected by pattern matching the position of the vascular wall in each frame based on the amplitude information of the reception signals outputted from the ultrasound probe when the first ultrasonic beam is transmitted and received.

7. The ultrasound diagnostic method according to claim 5, wherein the vascular wall expansion/contraction direction is detected by detecting a boundary between a blood vessel lumen and the vascular wall based on the amplitude information of the reception signals outputted from the ultrasound probe when the first ultrasonic beam is transmitted and received and detecting a direction substantially perpendicular to the detected boundary as the vascular wall expansion/contraction direction.

8. The ultrasound diagnostic apparatus according to claim 5, wherein when the vascular wall moves in a direction perpendicular to the vascular wall expansion/contraction direction associated with a heartbeat, the vascular wall movement is tracked using the amplitude information and the phase information of the reception signals corresponding to respective positions preceding and following the movement.

9. The ultrasound diagnostic apparatus according to claim 5, wherein an ultrasound image is produced based on the reception signals outputted from the ultrasound probe when the first ultrasonic beam is transmitted and received.

* * * * *